US005693533A

United States Patent [19]
Raney et al.

[11] Patent Number: 5,693,533
[45] Date of Patent: Dec. 2, 1997

[54] HUMAN BREAST CARCINOMA CELL LINE CAPABLE OF PRODUCTION OF A SPONTANEOUSLY METASTASIZING TUMOR IN ANIMALS FOR USE IN ANTICANCER DRUG TESTING

[75] Inventors: Shula Raney, Fort Lauderdale; Dennis Emma, Miramar; Josephine Hurst, Fort Lauderdale, all of Fla.

[73] Assignee: The Goodwin Institue for Cancer Research, Plantation, Fla.

[21] Appl. No.: 350,938

[22] Filed: Dec. 7, 1994

[51] Int. Cl.$^6$ .................................................. C12N 5/08
[52] U.S. Cl. ................................................................ 435/366
[58] Field of Search ................................. 435/240.2, 366; 429/93.1

[56] References Cited

PUBLICATIONS

Hurst et. al 1993 Br. J. Cancer 68:274–276.
Schwartz, M.K. 1994 In. Antigen & Antibody Molecular Engineering in Breast Cancer Diagnosis & Treatment (ed.) R.L. Ceriani pp. 41–53, Plenum Press. N.Y.

*Primary Examiner*—James Ketter
*Assistant Examiner*—Irem Yucel
*Attorney, Agent, or Firm*—Saliwanchik, Lloyd & Saliwanchik

[57] ABSTRACT

An adherent, stable, continuous human breast carcinoma cell line (GI-101A) has been produced from an infiltrating ductal breast carcinoma xenograft (GI-101) which has been grown and maintained in athymic mice for the past nine years. The GI-101A cells grow with an average doubling time of about 48 to about 72 hours. The cells display antigenic determinants consistent with those of the human breast tumor xenograft (GI-101) from which it was derived. The cell line, GI-101A, when injected subcutaneously into the subaxial area of athymic animals, such as athymic mice, produces tumors that spontaneously metastasize to distant organ sites, such as the lungs and lymph nodes. The cell line and the tumors that it produces may be used as model systems for study mechanisms responsible for metastatic behavior and for testing for new as well as screening for effective new anti-cancer drug therapies.

2 Claims, No Drawings

HUMAN BREAST CARCINOMA CELL LINE CAPABLE OF PRODUCTION OF A SPONTANEOUSLY METASTASIZING TUMOR IN ANIMALS FOR USE IN ANTICANCER DRUG TESTING

FIELD OF THE INVENTION

This invention relates to the fields of tumor cell biology, metastasis research, immunochemistry, molecular biology, and anticancer drug development and screening. More particularly, the present invention is concerned with a stable metastatic human breast carcinoma cell line that is suitable for in vitro and in vivo anticancer drug development and screening.

BACKGROUND

The 1992 cancer statistics estimated that 181,000 new cases of invasive breast would be diagnosed that year and result in 46,300 new deaths. See Boring, C. C. et al.: *Cancer,* 42:19 (1992). In North America, breast cancer is the most common malignancy of women and accounts for 27% of all female cancers and 18% of all female cancer mortalities. For women aged 40-55, breast cancer represents the leading cause of death overall. While the age standardized incidence of breast cancer has risen annually (1-4% per year), the age adjusted mortality has remained stable for the past fifty years (in the U.S.A.). Most women that die from breast cancer succumb not to the original primary disease, which is usually amenable to various therapies, but rather from metastatic spread of the breast cancer to distant sites. This fact underscores the need to develop either novel anticancer agents or more aggressive forms of therapy directed specifically against the metastatic breast tumor cell. Requisite to the development of new treatment modalities is a fundamental, thorough understanding of the regulatory processes inherent to the growth of both the primary and metastatic breast cancer cell and tumor. This process has been severely hampered by the lack of appropriate and clinically relevant modeling systems. The model described here can be useful in providing the latter.

Anticancer drug screening trials have been conducted for many years using a wide variety of tumor cell lines as targets. Drugs that show anticancer activity in vitro are subsequently tested against an in vivo tumor model. While there are, in all, a large number of human tumor cell lines, the availability of human breast cancer cell lines is limited. Of the few human breast tumor cell lines that are even capable of producing a tumor in immune suppressed animals, fewer still are capable of producing a metastasizing tumor in the animal except under extreme forms of manipulation. Cell lines like MDA-MB-231 and MDA-MB-435, see Price, J. E. et al.; *Cancer Res.,* 50:717-721 (1990), produce consistently metastasizing tumors when the cells are injected directly into the mammary fat pad of animals, such as athymic mice. On the other hand, subcutaneous injection of these cells produce tumors that are less consistently metastatic and have a different metastatic pattern than tumors implanted directly to the mammary fat pad. What is needed are cells that can produce a metastasizing tumor without the need for surgical or experimental manipulations. The invention (GI-101A) described here, as well as the xenograft line from which it was derived, consistently produce tumors and lung metastases from subcutaneous implants, thus requiring no additional experimental manipulations.

The Goodwin Institute for Cancer Research has previously developed and reported a spontaneously metastasizing human breast tumor xenograft model (GI-101). See Hurst, J. et al.: *Cancer,* 68:274-276 (1993). This solid tumor model, maintained through serial animal transplantation, has been described in detail. In brief, the tumor presents as a poorly differentiated mammary carcinoma with occasional acinar and ductal formation. The tumor xenograft when implanted subcutaneously grows slowly and eventually metastasizes to the lungs, lymph nodes and bone marrow of athymic murine recipients. This invention is the development of a cell line (GI-101A) from the GI-101 xenograft that is suitable for both in vitro and in vivo investigations.

SUMMARY OF THE INVENTION

The present invention overcomes certain of the above-mentioned shortcomings and drawbacks and is directed to a novel, stable, continuous, human aneuploid breast carcinoma cell line which has the ability to produce metastatic solid tumors at distant organ sites, such as the lungs and lymph nodes, when introduced into athymic nude animals, like athymic nude mice. Surprisingly, the cell line of the present invention is able to consistently produce solid tumors and lung metastases from subcutaneous and/or injected implants without requiring additional experimental manipulations. Moreover, the cell line of the present invention constitutes a unique system that is suitable for detecting and screening for new and effective anti-cancer therapies. This may be accomplished by, for instance, introducing into an athymic nude animal having the cell line of the present invention introduced therein, a drug in an effective amount and analyzing the animal to determine the effectiveness of the drug against one or more or all of the solid tumor metastases produced in the animal by the cell line at the distant organs.

While the present invention is described herein with reference to the particular cell line disclosed, it should nevertheless be understood that those skilled in this art that the present invention contemplates equivalents to the cell line which have identical or substantially similar characteristics and activity. Therefore, the present invention includes any cell line which has the ability to accomplish the objectives of the instant invention, i.e., any human aneuploid breast carcinoma cell line having a panel of human and tumor markers as identified in Table I below which, when implanted or injected into an athymic nude animal, produces solid tumor metastases at distant organ sites, such as the lungs and the lymph nodes, and may be used as in vivo and in vitro model systems to detect and screen for new and effective anti-cancer therapies.

The above features and advantages of the present invention will be better understood with reference to the accompanying Detailed Description. It should also be understood that the particular methods and cell lines illustrating the invention are exemplary only and are not to be regarded as limitations of the present invention.

DETAILED DESCRIPTION OF THE INVENTION

The cell line is derived from a human breast tumor xenograft line (GI-101) which originates as a recurrent infiltrating ductal mammary adenocarcinoma of a 57 year old female (Stage IIIa, T3N2MX). This xenograft line is poorly differentiated and presents with occasional ductal and acinar formation. The tumor line is grown and maintained through serial animal transplantation in athymic mice for over nine years.

Tumor xenograft material is asceptically harvested from an animal bearing the GI-101 breast tumor xenograft

[transplant generation #21; tumor volume>2000 mm$^3$]. The xenograft is then dissected of connective and fatty tissue and gross necrotic areas and the remaining tissue mechanically dissociated through a 200 mesh sterile stainless steel cell sieve (Sigma) into RPMI 1640 tissue culture medium (Sigma) containing 10% fetal calf serum (Flow) and supplemented with 200 mM glutamine and 50 ug/ml of gentamycin (Sigma). The tumor brie is washed three times in phosphate-buffered saline at 150×g to remove dead cells. Viable cell counts are made and the cells seeded (1×10$^6$ cells/ml) in 5 ml of tissue culture medium, as described above, in 25 cm$^2$ tissue culture flasks and incubated at 37° C., 5% $CO_2$ in air and 99% relative humidity. The cultures are demi-fed weekly with fresh media and recharged bi-weekly for eight weeks with fresh tumor cells using the same procedure outlined above for obtaining the original tumor brie. The cultures are maintained as an adherent cell line, removing non-adherent cells for each subculture. Subcultures are performed by detaching adherent cells with 0.05% trypsin-EDTA (Sigma). As soon as cells are detached, cell viability in number are counted and the cells seeded as described above. Fibroblasts disappear after three months of continuous culture following cessation of the last tumor cell recharge. Upon fresh culture, the cells (GI-101A) grow with a lag phase of about 48 to about 72 hours followed by a doubling time of approximately sixty hours. In culture, the cells grow as sheets of epithelial-like cells, which may pile up into spherical colonies after the culture reaches confluency.

The tumorigenicity of the GI-101A cells is originally confirmed by injecting 60×10$^6$ cells from in vitro passage #6 into the subcutaneous subaxillary area of five 10 week-old female athymic nude mice. Before injection, the cells are treated with EDTA (200 ug/ml) to detach them from the tissue culture flask. The cells are then washed three times by centrifugation at 400×g and resuspended in serum-free RPMI 1640 tissue culture medium for injection. The histology of the primary tumors produced from injection of GI-101A cells result in moderate to well differentiated tumors showing lymphocyte infiltration and some areas of necrosis. Serial transplantation of these tumors results in tumors with the same growth characteristics as the original GI-101 xenograft and display a progressive loss of differentiation as the proportion of murine stromal elements increases with each transplant generation. By the third serial transplantation, the tumors derived resemble the original GI-101 xenograft. The tumors produced by injection of GI-101A tumor cells and subsequent serial transplantation spontaneously metastasize distant organ sites, such as the lungs and lymph nodes.

The cell line is believed to be human and aneuploid by histogram analysis. Two major cell populations are apparent.

In addition, the cell line is characterized for a panel of human and tumor markers, as reported in Table I by the methods listed below.

TABLE I

| Marker | Description | Reactivity* | Method of Analysis** |
|---|---|---|---|
| MC5 | Breast Tumor Antigen | +++ | F,H |
| CEA | Carcinoembryonic Antigen | +++ | F,H |
| CK | Cytokeratin (human) | ++++ | F,H |
| PCNA | Proliferating Cell Nuclear Antigen | ++ | F,H |
| P120 | Proliferation Antigen | +++ | F,H |
| P105 | Proliferation Antigen | +++ | F |

TABLE I-continued

| EGF-r | Epidermal Growth Factor Receptor | +++ | F,H |
|---|---|---|---|
| EMA | Epithelial Membrane Antigen | ++ | F,H |
| KC4 | Cytokeratin (human) | +++ | H |
| LAM | L-Selectin Adhesion Molecule | +/− | F |
| VCAM | Vascular Cell Adhesion Molecule | − | F |
| ELAM | Endothelial Leukocyte Adhesion Molecule | − | F |
| ICAM | Intercellular Adhesion Molecule | + | F |
| IL-2r(p75) | Interleukin 2 Receptor (mw = 75 kD) | − | F |
| IL-2r(p55) | Interleukin 2 Receptor (mw = 55 kD) | − | F |
| CD15 | Neutrophil Marker | ++ | F |
| CD45 | Monocyte Marker | − | F |
| CD38 | Activated Lymphocyte/Basophil/Monocyte Marker | − | F |
| CD34 | Immature Granulocyte Marker | − | F |
| APO-1 | Apoptosis 1 Marker | − | F |
| FEL | Leukemia associated oncogene | + | P |
| NM23 | Metastasis Associated Marker | − | P |
| MDM2 | Suppressor of p53 oncogene | ++ | H,W |
| TGF-a | Transforming Growth Factor alpha | ++ | E,H |

*Reactivity    *Method of Analysis

| − | = | None | E | = | ELISA |
|---|---|---|---|---|---|
| + | = | Low–Moderate | F | = | Flow Cytometry |
| ++ | = | Moderate | H | = | Immunocytochemistry |
| +++ | = | Moderate–High | P | = | Polymerase Chain Reaction |
| ++++ | = | High | W | = | Western Blot |

Commercial kits as prepared by Oncogene Science are used to determine the levels and expression of TGF-a.

Cytospin slides prepared using the GI-101A cells are prepared and stained with biotinylated primary monoclonal antibody (i.e., EGF, etc.), followed by streptavidin conjugated peroxidase with ABTS/$H_2O_2$ (2,2'Azino-di-(3-Ethylbenzthiozoline Sulfonic acid) as a substrate chromogen. The slides are counter stained with hematoxylin and eosin.

Flow cytometric analysis for proliferation associated nuclear or cell surface antigens are performed by the methods reported in Bolton, et al. See Bolton, W. E. et al.; Cytometry, 13(2):117–126 (1992). Briefly, whole cells or nuclei (prepared by Coulter DNA-Prep) are incubated with 10 ug of specific antibody (PCNA, etc.). Following lysis and propidium iodide staining (for nuclei) or washing, the cells are analyzed using an upgraded Profile I Flow Cytometer (Coulter Corp., Hialeah, Fla.) fitted with an argon laser and equipped with an EPICS ELITE workstation using the Multicycle software analysis package developed by P.S. Rabinovitch (Phoenix Flow Systems, San Diego, Calif.). DNA histograms for all cell preparations are constructed along with data analysis for percentage of positive cells and stain intensity for those cells.

The gene expression for Fel is analyzed using PCR primers identifying previous work. Total RNA is isolated, first strand cDNAs synthesized using BRL/Gibco Superscript reverse transcriptase, and target sequences amplified with Taq DNA polymerase under manufacturers' directions. Strict quantitative analysis is first performed on human β-actin and transferrin receptor expression by constructing competitors as follows: Amplification of non-relevant sequence (FEL cDNA from B-ALL) with primers containing extended regions of β-actin or transferrin receptor homology. Those competitor constructs are cloned into a bluescript vector (SK−) containing a 3' $A_{(20)}$ cassette. The competitor plasmids are then linearized and "mRNA" transcribed with a Promega Ribomax transcription kit and T7 RNA polymerase, and isolated using an Invitrogen micro-fast-tract poly A isolation kit. Poly A RNA is then spectrophotometrically quantitated, and known amounts added to total tumor RNA samples. These samples are then amplified with β-actin and transferrin receptor sequences, and both endogenous and competitor PCR products (300–500 bp) will be quantitated visually on ethidium stained 3% nusieve agarose TAE gels. Subsequent semi-quantitative analysis on metastasis associated gene expression will standardize against these internal controls by including β-actin and/or transferrin receptor primers in each amplification reaction.

MDM2 expression is detected by SDS poly-acrylimide gel electrophoresis of the GI-101A cells. Electrophoresis is performed using a Bio-Rad Protein II electrophoresis system. After electrophoresis, the proteins are transferred to nitrocellulose membranes using a Bio-Rad Trans Blot cell. The membranes are blocked to reduce non-specific protein binding and MDM2 detected using a specific anti-MDM2 monoclonal antibody. The labeled bands on the nitrocellulose membranes are visualized by treatment with horseradish peroxidase conjugated secondary antibody and detected by enhanced chemiluminescence techniques (Amersham, Rockford, Ill.).

While the invention has been described with reference to a preferred embodiment, it should be understood by those skilled in the art that various changes may be made and equivalents may be substituted for elements thereof without departing from the scope of the invention. For instance, the cell line or equivalents thereto may be used as model systems for studying mechanisms responsible for metastatic behavior and for testing and screening anti-cancer drug therapies in other suitable animals, such as canines, bovines, rabbits, rats, pigs, sheep and the like. In addition, many modifications may be made to adapt a particular situation or material to the teachings of the invention without departing from the essential scope thereof. Therefore, it is intended that the invention not be limited to the particular embodiment disclosed as the best mode contemplated for carrying out the invention, but that the invention will include all embodiments falling within the scope of the appended claims.

Having described our invention, we claim:

1. A human aneuploid breast carcinoma in vitro cell line wherein said cell line produces a solid carcinoma upon subcutaneous implantation or injection into an immune deficient animal, said cell line further having the following marker profile:

a.) positive for breast tumor antigen (MC-5), carcinoembryonic antigen (CEA), proliferating cell nuclear antigen (pCNA), proliferation antigens (p120 and p105), epidermal growth factor receptor (425 and 528), and human cytokeratins (KC4), epithelial membrane antigen (EMA), neutrophil marker (CD 15), p53 oncogene suppressor protein (MDM2), transforming growth factor alpha (TGF-a), L-selectin adhesion molecule (LAM), intercellular adhesion molecule (ICAM), and leukemia associated oncogene (FEL, and b.) negative for vascular cell adhesion molecule (VCAM), endothelial leukocyte adhesion molecule (ELAM), interleukin 2 receptors (IL-2p75 and IL-2p55), monocyte marker (CD45), activated lymphocyte/basophil/monocyte marker (CD38), immature granulocyte marker (CD34), apoptosis 1 marker (APO-1), and non-metastasis associated gene (NM23).

2. A human aneuploid breast carcinoma cell line designated as GI-101A, wherein said cell line is stable in vitro.

* * * * *

UNITED STATES PATENT AND TRADEMARK OFFICE
CERTIFICATE OF CORRECTION

PATENT NO. : 5,693,533

DATED : December 2, 1997

INVENTOR(S) : Shula Raney, Dennis Emma, Josephine Hurst

It is certified that error appears in the above-indentified patent and that said Letters Patent is hereby corrected as shown below:

Column 5, line 22, insert the following:

-- Cultures containing the subject GI-101A cell line have been deposited in the permanent collection of the American Type Culture Collection (ATCC), 12301 Parklawn Drive, Rockville, Maryland 20852 USA on October 22, 1997. The accession number for GI-101A is ATCC CRL-12420.

The subject culture has been deposited under conditions that assure that access to the culture will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, *i.e.*, it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.--

UNITED STATES PATENT AND TRADEMARK OFFICE
CERTIFICATE OF CORRECTION

PATENT NO. : 5,693,533

DATED : December 2, 1997

INVENTOR(S) : Shula Raney, Dennis Emma, Josephine Hurst

It is certified that error appears in the above-indentified patent and that said Letters Patent is hereby corrected as shown below:

Column 6, line 31, Claim 2: After "GI-101A" insert -- (ATCC CRL-12420) --.

Signed and Sealed this

Fourth Day of August, 1998

Attest:

BRUCE LEHMAN

Attesting Officer

Commissioner of Patents and Trademarks